(12) United States Patent
Okuda et al.

(10) Patent No.: US 8,100,451 B2
(45) Date of Patent: Jan. 24, 2012

(54) MULTI-FINGERED ROBOT HAND

(75) Inventors: Akinobu Okuda, Osaka (JP); Osamu Mizuno, Osaka (JP); Tohru Nakamura, Osaka (JP)

(73) Assignee: Panasonic Corporation, Osaka (JP)

( * ) Notice: Subject to any disclaimer, the term of this patent is extended or adjusted under 35 U.S.C. 154(b) by 492 days.

(21) Appl. No.: 12/376,536

(22) PCT Filed: Oct. 24, 2007

(86) PCT No.: PCT/JP2007/070685
§ 371 (c)(1),
(2), (4) Date: Feb. 5, 2009

(87) PCT Pub. No.: WO2008/062625
PCT Pub. Date: May 29, 2008

(65) Prior Publication Data
US 2010/0176615 A1    Jul. 15, 2010

(30) Foreign Application Priority Data

Nov. 24, 2006  (JP) ................................ 2006-316877
Sep. 11, 2007  (JP) ................................ 2007-235467

(51) Int. Cl.
*B25J 15/10* (2006.01)
(52) U.S. Cl. ..................... 294/106; 294/119.3; 294/213; 901/39
(58) Field of Classification Search .................. 294/106, 294/111, 119.3, 213, 902; 901/38, 39; 623/63, 623/64
See application file for complete search history.

(56) References Cited

U.S. PATENT DOCUMENTS

| | | | | |
|---|---|---|---|---|
| 3,694,021 A | * | 9/1972 | Mullen | 294/106 |
| 3,727,968 A | * | 4/1973 | Tsuchihashi et al. | 294/198 |
| 4,364,593 A | * | 12/1982 | Maeda | 294/106 |
| 4,367,891 A | * | 1/1983 | Wauer et al. | 294/197 |
| 4,986,723 A | * | 1/1991 | Maeda | 414/729 |
| 5,245,885 A | * | 9/1993 | Robertson | 74/490.01 |
| 5,447,403 A | * | 9/1995 | Engler, Jr. | 414/4 |

(Continued)

FOREIGN PATENT DOCUMENTS

JP        4-189493        7/1992

(Continued)

OTHER PUBLICATIONS

International Search Report issued Dec. 4, 2007 in the International (PCT) Application No. PCT/JP2007/070685.

(Continued)

*Primary Examiner* — Dean Kramer
(74) *Attorney, Agent, or Firm* — Wenderoth, Lind & Ponack, L.L.P.

(57) ABSTRACT

A multi-fingered robot hand has a minimum required number of joints in finger mechanisms and is capable of stably grasping a variety of articles. The multi-fingered robot hand includes: a first palm portion provided with three finger mechanisms each connected by a root joint; a second palm portion provided with one finger mechanism connected by a root joint; and a palm joint connecting the first palm portion and the second palm portion. The palm joint permits a variation in the connection angle of the second palm portion to the first palm portion. The palm joint, bending joints, bending joints of the root joints and the root joint have rotation axes parallel to each other, and the finger mechanisms bend while turning around the rotation axes.

14 Claims, 16 Drawing Sheets

U.S. PATENT DOCUMENTS

| | | | |
|---|---|---|---|
| 6,217,094 B1 * | 4/2001 | Hanaduka et al. | 294/106 |
| 7,370,896 B2 * | 5/2008 | Anderson et al. | 294/106 |
| 2005/0121929 A1 * | 6/2005 | Greenhill et al. | 294/106 |

FOREIGN PATENT DOCUMENTS

| | | |
|---|---|---|
| JP | 11-156778 | 6/1999 |
| JP | 2004-351567 | 12/2004 |
| JP | 2006-992 | 1/2006 |
| JP | 2006-26875 | 2/2006 |
| JP | 2006-116667 | 5/2006 |
| WO | 03/080297 | 10/2003 |

OTHER PUBLICATIONS

Chinese Office Action issued Oct. 12, 2010 in Application No. 200780028899.6.

* cited by examiner

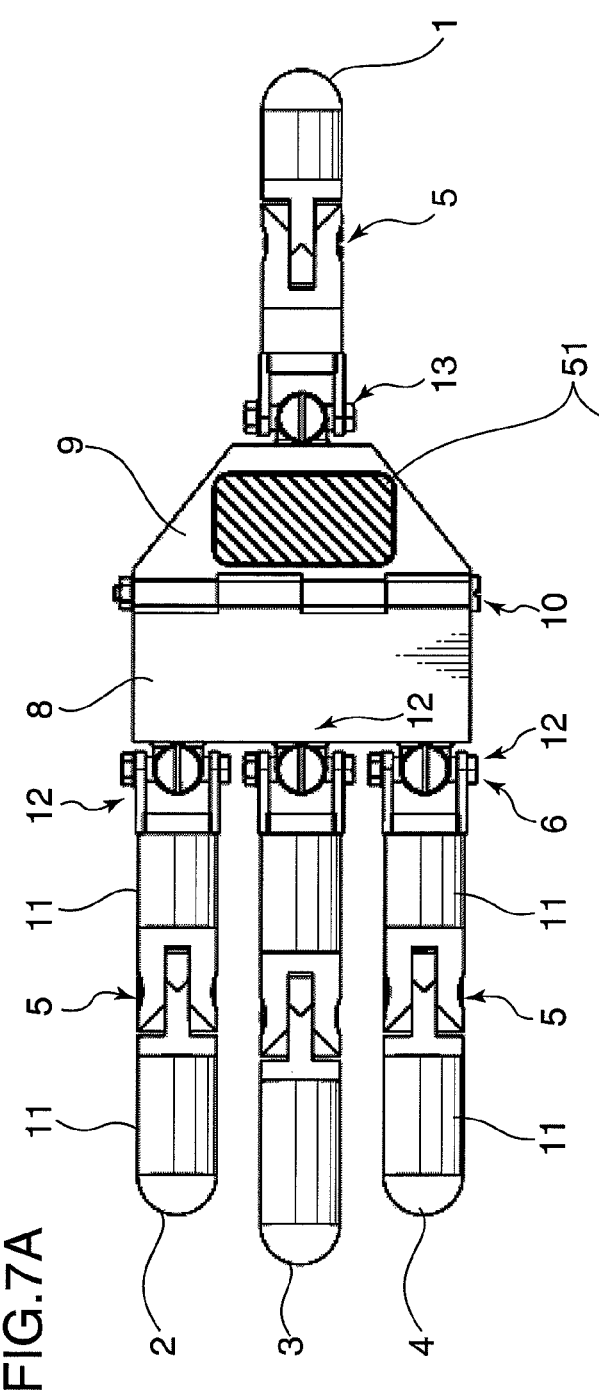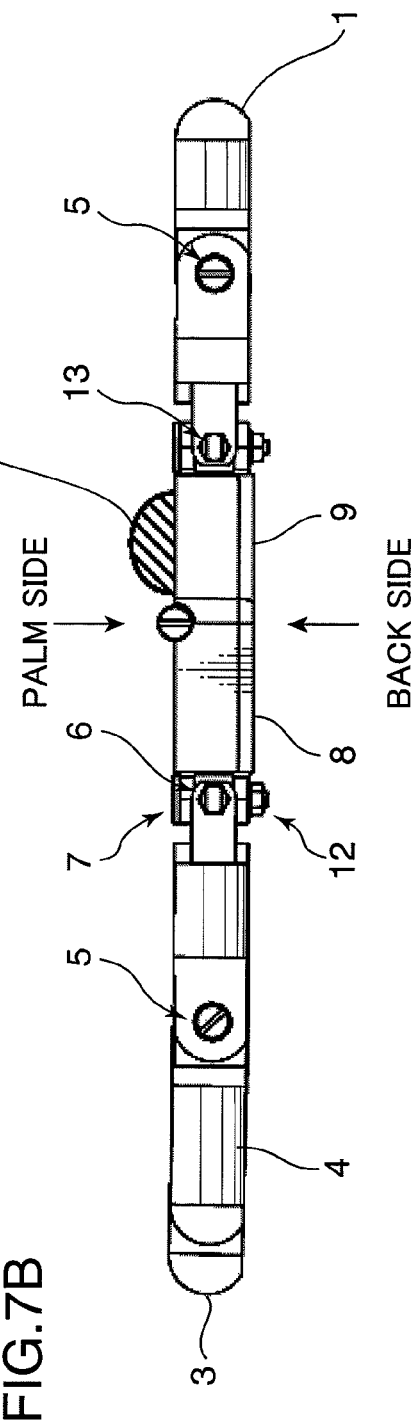
FIG.7A
FIG.7B

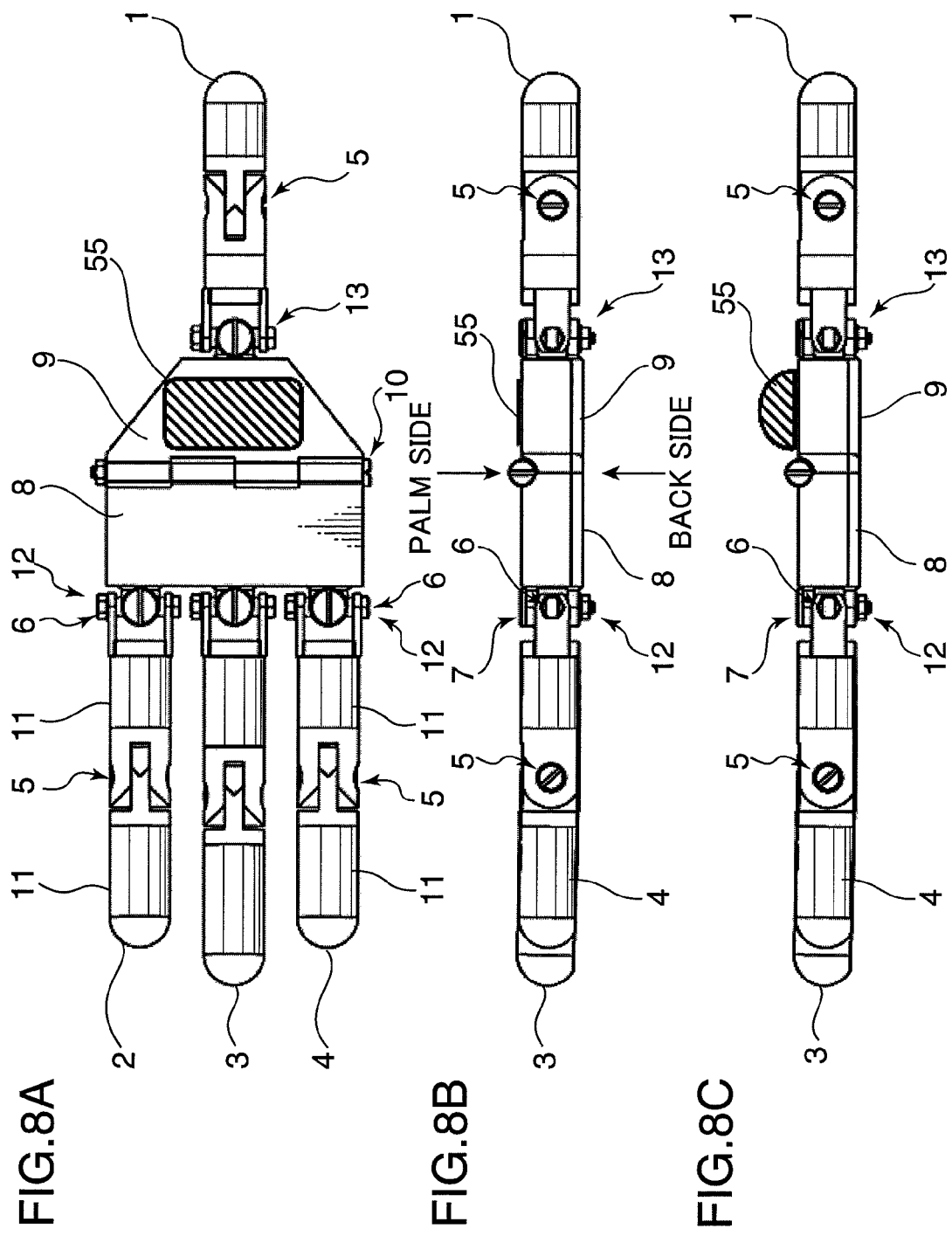

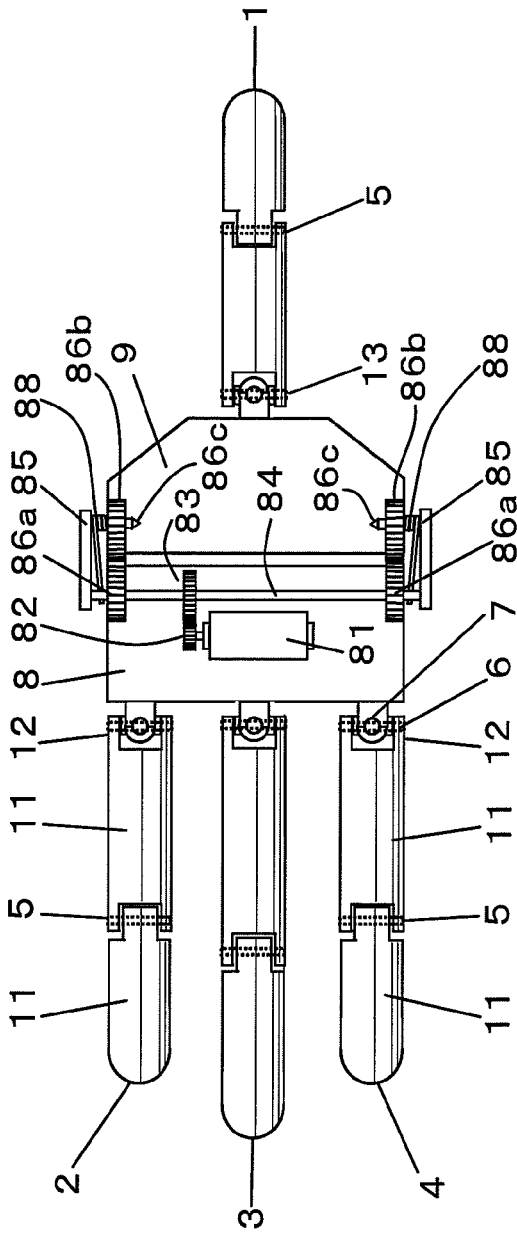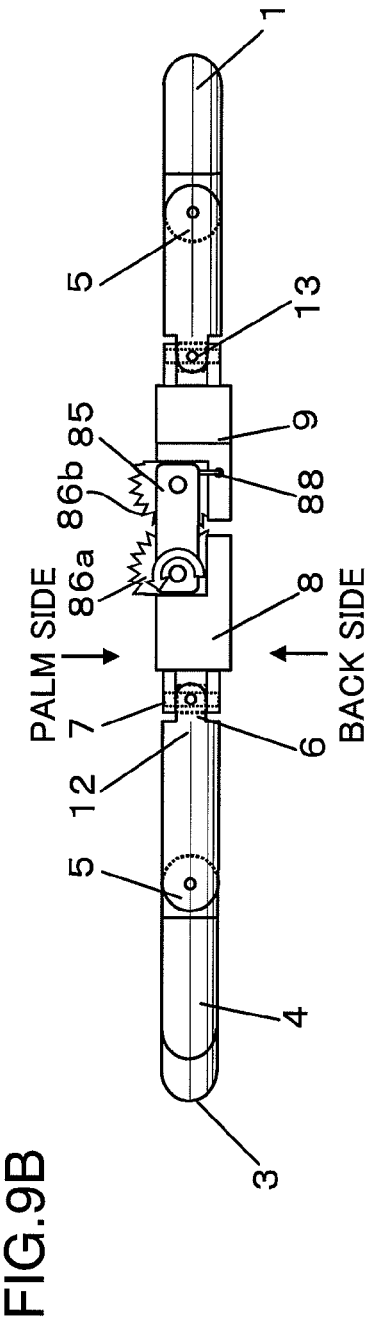
FIG.9A
FIG.9B

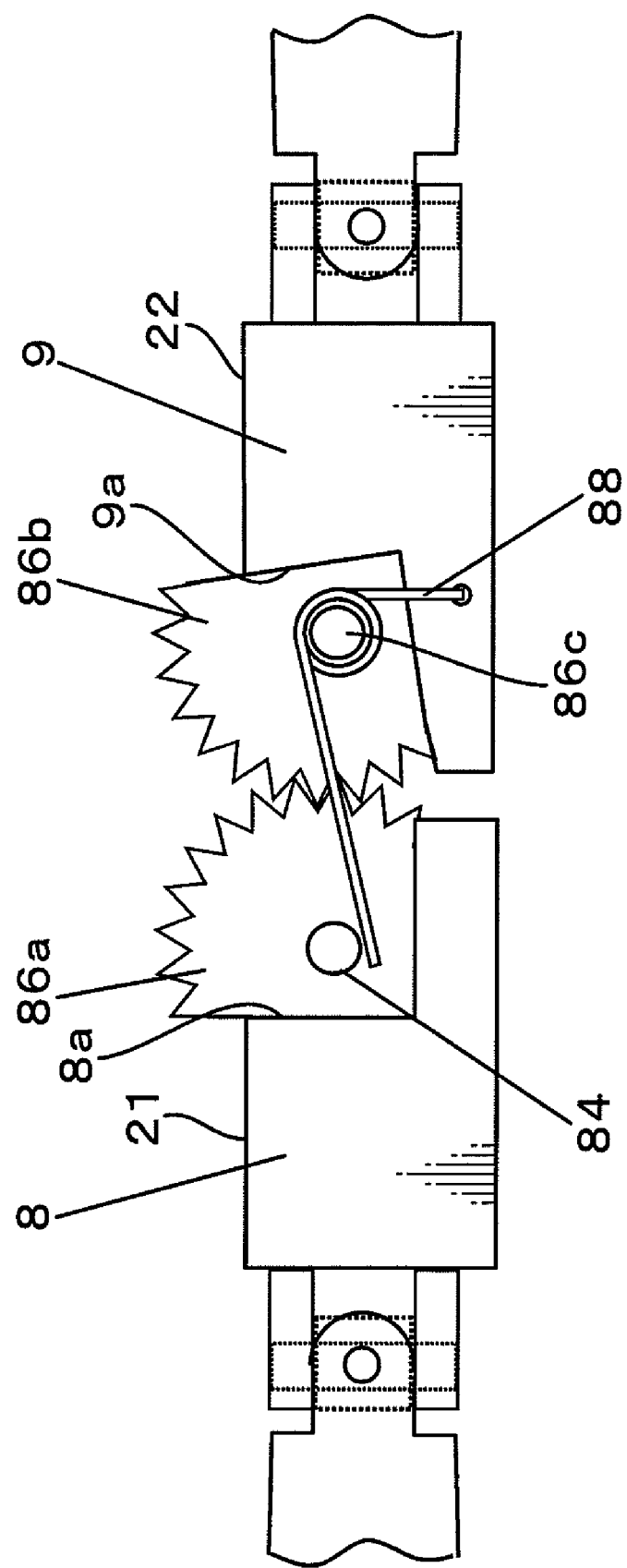

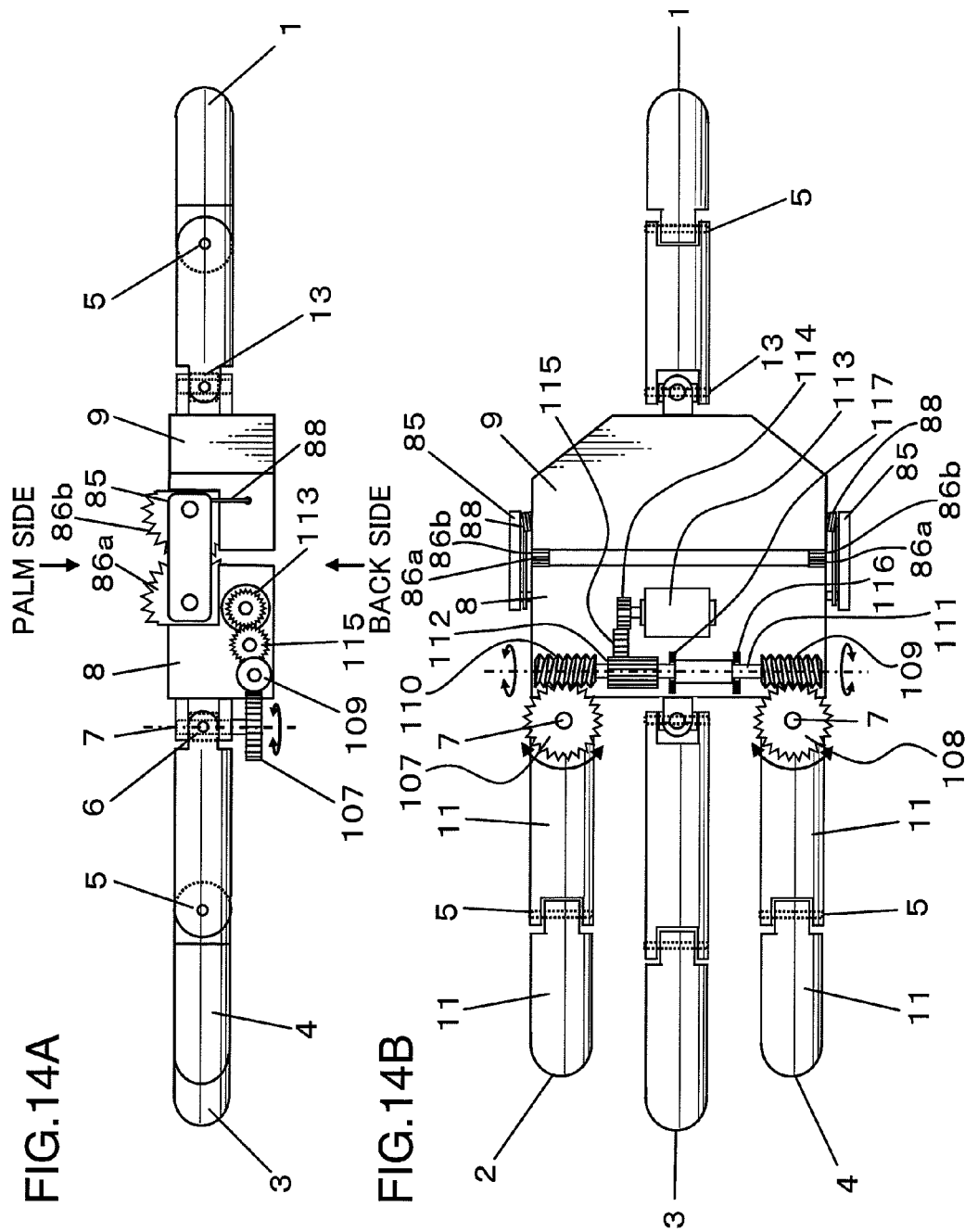

MULTI-FINGERED ROBOT HAND

BACKGROUND OF THE INVENTION

(1) Field of the Invention

The present invention relates to a robot, particularly, a multi-fingered robot hand grasping and manipulating a variety of articles.

(2) Description of Related Art

The recent declining birthrate and aging population is expected to cause a labor shortage and an aged society, thereby producing a great demand for industrial and household robots. Particularly, a robot hand capable of grasping a variety of articles skillfully and stably is indispensable for doing complicated work and is expected to be applied to an artificial hand for a physically handicapped person. Taking the situation into account, a number of human-like robot hands having a similar structure to a human hand were put forward.

FIGS. 15A and 15B show a human-like robot hand with a built-in motor capable of making a similar motion to a human hand (e.g., refer to Patent Document 1). As shown in FIG. 15A, a finger mechanism 60 includes three bending joints 61, 62 and 63 and an open-close joint 64 perpendicular to the bending joint 63, and each joint is driven by motors 65, 66, 67 and 68. FIG. 15B shows five finger mechanisms 60 and 70 attached to a palm portion 69. The finger mechanisms 70 are designed to move with the bending joints 61 and 62 of the finger mechanism 60 interlocked by a four-joint link mechanism.

Furthermore, in order to grasp articles in various shapes more stably, some robot hands having a human-like ball of the thumb were also proposed.

FIG. 16 shows a robot hand provided with a ball of the thumb bulging as the thumb turns in the same manner as a human hand (e.g., refer to Patent Document 2). As shown in the figure, a robot 71 includes a ball of the thumb 73 and a palm portion 74 arranged in a robot-hand base 72, and the ball 73 bulges from the surface of the palm portion 74 as a finger mechanism 75 corresponding to the thumb turns to the side of the palm portion 74 shown by an arrow 76.

Patent Document 1: Japanese Patent Laid-Open Publication No. 11-156778

Patent Document 2: Japanese Patent Laid-Open Publication No. 2004-351567

However, the conventional human-like robot hand shown in FIGS. 15A and 15B has the following problems. This robot hand includes a palm portion having a so-called single-plate shape to thereby grasp an article by bringing only the tip of a finger mechanism and a part of the palm portion into contact with the article. This means that the robot hand comes in contact with the article in a small area, thereby making its holding unstable, depending upon the shape or size of the article. In addition, this robot hand has a degree of freedom great enough for grasping, but it has many joints in each finger mechanism, thereby making harder in embedding mechanisms driving them compactly therein and thus making the robot hand larger or heavier. Besides, many such joints need to be controlled, thereby making the control extremely complex.

The conventional robot hand provided with a ball of the thumb shown in FIG. 16 has a problem as follows. This robot hand cannot stably grasp a plate-shaped article such as a dish plate because the bulging ball of the thumb itself is not supposed to sandwich the article.

BRIEF SUMMARY OF THE INVENTION

In order to solve the above problems, it is an object of the present invention to provide a multi-fingered robot hand having a minimum required number of joints in finger mechanisms and capable of stably grasping a variety of articles.

A multi-fingered robot hand according to an aspect of the present invention includes: a first palm portion provided with at least two finger mechanisms each connected by a first root joint; a second palm portion provided with at least one finger mechanism connected by a second root joint; and a connecting portion connecting the first palm portion and the second palm portion, in which the connecting portion permits a variation in the connection angle of the second palm portion to the first palm portion.

BRIEF DESCRIPTION OF THE DRAWINGS

FIGS. 7A and 7B are front and side views, respectively, of a multi-fingered robot hand according to a second embodiment of the present invention.

FIGS. 8A to 8C are front and side views showing a bag member deflated and inflated, respectively, in a multi-fingered robot hand according to a third embodiment of the present invention.

FIGS. 9A and 9B are front and side views, respectively, of a multi-fingered robot hand according to a fourth embodiment of the present invention.

FIG. 11 is a side view of a variation of the multi-fingered robot hand according to the fourth embodiment.

FIGS. 14A and 14B are side and front views, respectively, of a multi-fingered robot hand according to a sixth embodiment of the present invention.

DETAILED DESCRIPTION OF THE INVENTION

An embodiment of the present invention will be below described in detail with reference to the drawings.

First Embodiment

Figure 1A:
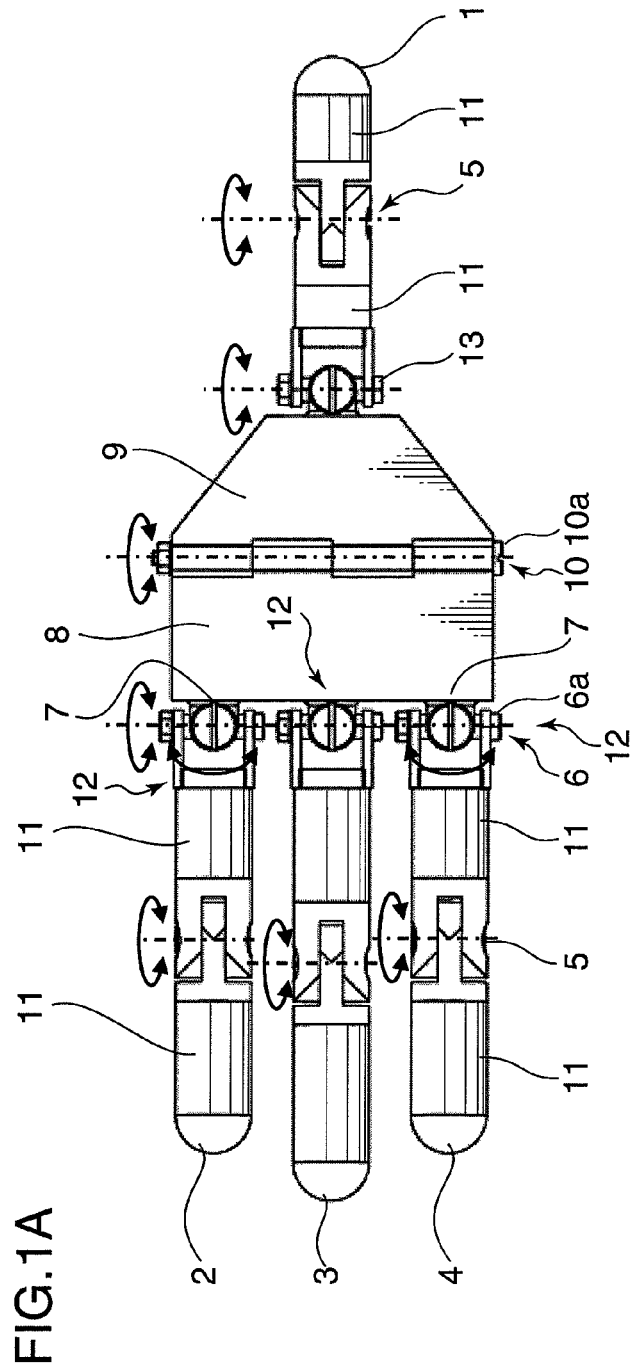
FIGS. 1A and 1B are front and side views, respectively, of a multi-fingered robot hand according to a first embodiment of the present invention.
Figure 1B:
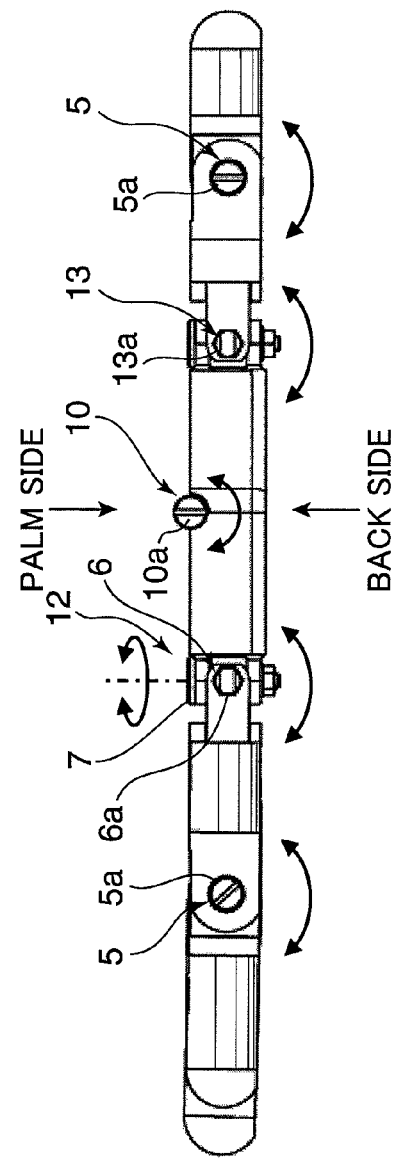

FIGS. 1A and 1B show a multi-fingered robot hand according to an embodiment of the present invention. As shown in the figure, the robot hand according to this embodiment includes four finger mechanisms 1, 2, 3 and 4. Three finger mechanisms 2, 3 and 4 (first finger mechanisms) thereof and the remaining finger mechanism 1 (second finger mechanism) grasp an object to be grasped from both sides. The finger mechanism 1 corresponds to the thumb; 2, the index finger; 3, the middle finger; and 4, the third finger.

The robot hand includes a first palm portion 8 provided with the finger mechanisms 2, 3 and 4 connected thereto, a second palm portion 9 provided with the finger mechanism 1 connected thereto, and a palm joint 10 as a connecting portion connecting the first palm portion 8 and the second palm portion 9. In this embodiment, the connecting portion includes the single palm joint 10, the first palm portion 8 is a rectangular flat plate and the second palm portion 9 is a trapezoidal flat plate.

The palm joint 10 has a rotation axis 10a around which the first palm portion 8 and the second palm portion 9 can be relatively turned, thereby changing the connection angle of the second palm portion 9 to the first palm portion 8. In other words, the palm of the robot hand can be folded and the angle of the second palm portion 9 to the first palm portion 8 freely adjusted. The rotation axis 10a of the palm joint 10 is arranged at one end (upper end of FIG. 1B) in the plate thickness directions of the side surfaces of the first palm portion 8 and the second palm portion 9 which face each other, thereby turning the first palm portion 8 and the second palm portion 9 only to the palm side from the state of FIG. 1B where both are flush with each other.

The finger mechanisms 2, 3 and 4 are each connected to the first palm portion 8 by a root joint 12 (first root joint). The root joint 12 is arranged in the surface (left-end surface of FIG. 1A) opposite to the connection surface of the first palm portion 8 to the palm joint 10, thus meaning that the left-end surface of the first palm portion 8 is a finger-mechanism attachment surface.

The finger mechanism 1 is connected to the second palm portion 9 by a root joint 13 (second root joint). The root joint 13 is arranged in the surface (right-end surface of FIG. 1A) opposite to the connection surface of the second palm portion 9 to the palm joint 10, thus meaning that the right-end surface of the second palm portion 9 is a finger-mechanism attachment surface.

The finger mechanisms 2, 3 and 4 are parallel to each other. In the state of FIG. 1B, the finger mechanisms 1 to 4 are flush with each other and the main axis of the finger mechanism 1 lies substantially on a line from extended from the main axis of the finger mechanism 3. When the second palm portion 9 turns around the rotation axis 10a with respect to the first palm portion 8, the main axis of the finger mechanism 3 is supposed to lie on a plane formed by a locus of the main axis of the finger mechanism 1. In short, the finger mechanism 1 and the finger mechanism 3 move substantially on the same plane with each other.

Figure 2:
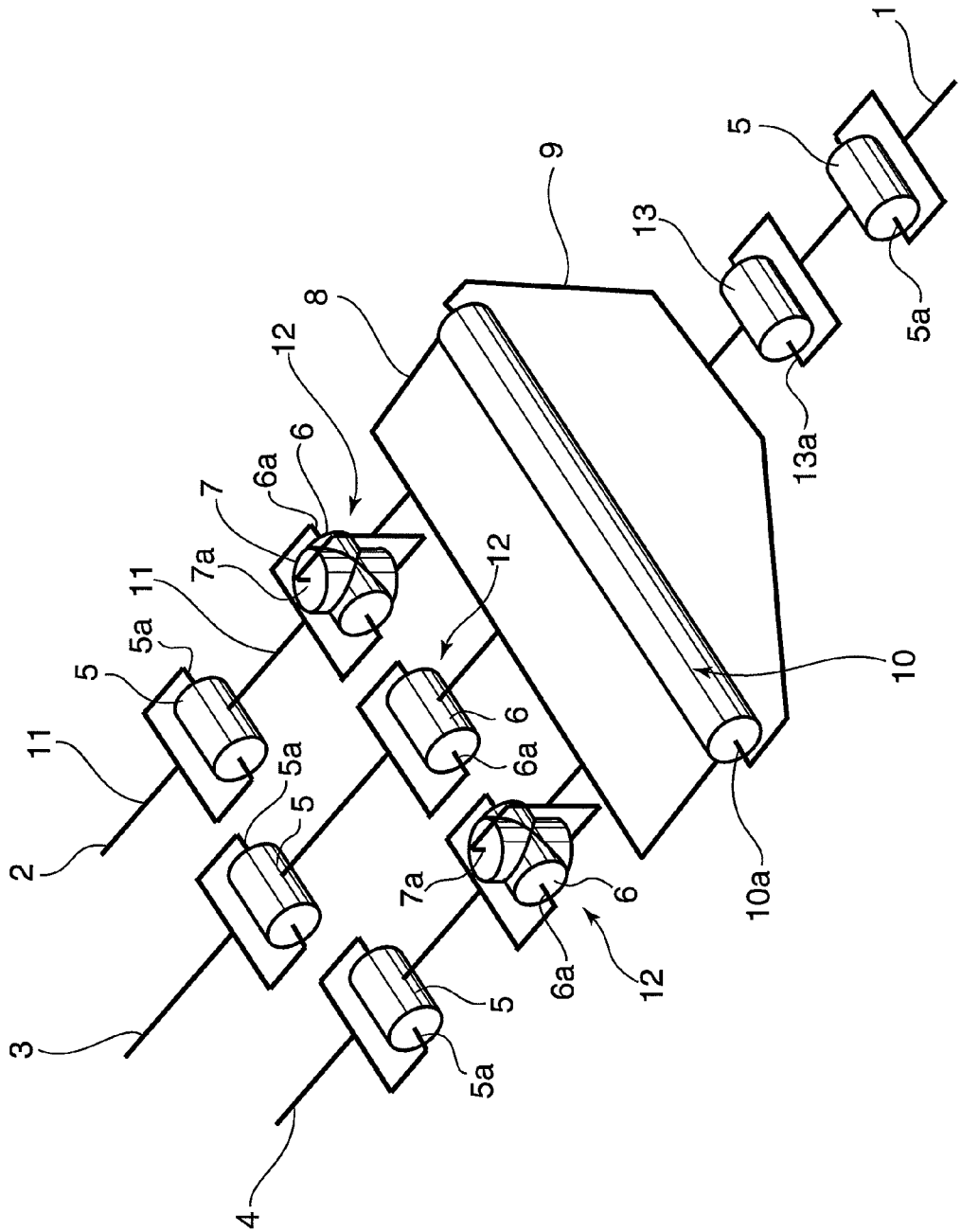
FIG. 2 is a perspective view showing a concept of joints of the multi-fingered robot hand according to the first embodiment.

As shown in FIG. 2 alike, each root joint 12 on the first-palm portion includes a bending joint 6 provided with a rotation axis 6a around which the first palm portion 8 and the finger mechanisms 2, 3 and 4 can be relatively turned. The bending joints 6 of the root joints 12 bend the finger mechanisms 2, 3 and 4 in the grasping direction.

The root joint 13 on the second-palm portion includes a rotation axis 13a around which the second palm portion 9 and the finger mechanism 1 can be relatively turned. In other words, the root joints 13 functions as a bending joint for bending the finger mechanism 1 in the grasping direction.

The rotation axes 6a of the root joints 12 on the first-palm portion and the rotation axis 13a of the root joint 13 on the second-palm portion are all parallel to the rotation axis 10a of the palm joint 10. As described earlier, the main axes of the finger mechanism 1 and the finger mechanism 3 are substantially flush with each other, thereby enabling their fingertips to face each other.

Each finger mechanism 1 to 4 includes a single bending joint 5 and two bone members 11, and specifically, is formed by connecting a tip-side bone member 11 and a root-side bone member 11 by the bending joint 5. The bending joint 5 is used for bending each finger mechanism 1 to 4 and has a rotation axis 5a arranged in the middle of each finger mechanism 1 to 4. The rotation axis 5a is parallel to the above rotation axes 10a, 6a and 13a, thereby enabling the finger mechanisms 1 and 3 to move substantially on the same plane with each other while bending.

The root joint 12 of each finger mechanism 2, 4 includes an open-close joint 7 for moving each finger mechanism 2, 4 perpendicularly to the bending directions of each finger mechanism 2, 4. The open-close joint 7 has a rotation axis 7a extending in the directions perpendicular to the rotation axes 5a, 6a, 10a and 13a, thereby enabling the finger mechanisms 2 and 4 at both right and left ends to turn perpendicularly (sideward) to the grasping direction. In other words, the finger mechanisms 2 and 4 can make an open-close motion in the directions where the adjacent finger mechanisms move close to or apart from each other or in the directions where they stretch laterally. It is desirable that the maximum right-and-left bending angle of the open-close joint 7 is approximately 20 to 30 degrees and that the maximum bending angle in the bending directions of the bending joint 5 and the root joints 12 and 13 is approximately 90 to 110 degrees, thereby offering an advantage in that the robot hand can grasp a variety of articles to be handled by a person.

The bending joint 5, the root joints 12 and 13 and the palm joint 10 are all designed to turn around the rotation axes 5a, 6a, 7a, 10a and 13a, respectively, by means of a pin connection. The bone members 11 are made of, for example, a light metal such as aluminum, engineering plastics such as an ABS (acrylonitrile-butadiene-styrene) resin, or the like.

As is not shown in any figure, the surface of each finger mechanism 1 to 4 excluding the joint and the surfaces of the first palm portion 8 and the second palm portion 9 supposed to come into contact with an article are covered with an elastic skin member having a uniform thickness. This gives a larger contact area in which each of them can contact and grasp an article and increases the friction thereof against an object to be held, thereby realizing more stable holding. The elastic skin member is made of, for example, rubber, urethane, silicone, sponge or the like. In this case, taking its good contact with an article into account, the elastic skin member may desirably have a rubber hardness of approximately 20 to 30 degrees in Hs (hardness spring). The elastic skin member may be formed in a single layer or several layers.

Furthermore, as is not shown in any figure, the bending joint 5 of each finger mechanism 1 to 4, each root joint 12, 13 and the palm joint 10 can be driven by a known art, for example, a gear driving method for driving each joint via a reduction mechanism or a differential mechanism by a motor embedded in the bone member 11, the first palm portion 8, the second palm portion 9 or the like, a wire driving method for driving each joint by giving a wire wound around each pulley (not shown) attached to each joint a pulling force by a motor or the like or a belt driving method for driving each joint by a belt such as a V-belt substituted for a wire, a link driving method for driving each joint by combining a motor and a link mechanism, or the like.

Moreover, as is not shown in any figure, the robot hand according to this embodiment is fixed to a robot manipulator on the back side of the first palm portion 8 shown in FIGS. 1A and 1B.

The thus configured multi-fingered robot hand grasping various articles in different manners will be below described with reference to schematic views shown in FIGS. 3 to 6.

Figure 3:
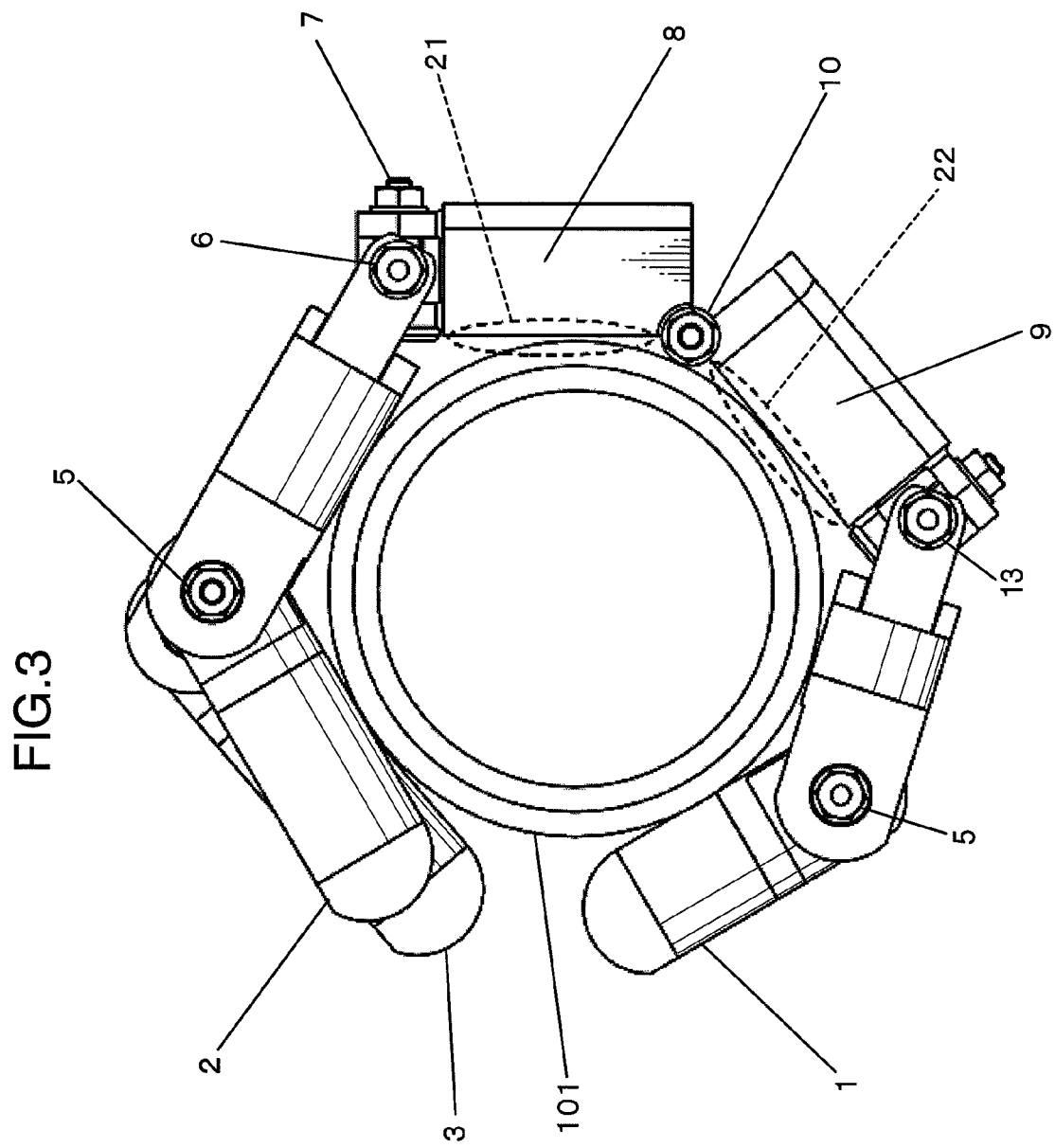
FIG. 3 is a side view showing the multi-fingered robot hand according to the first embodiment grasping a cylindrical cup.

First, FIG. 3 shows "grip holding"—the four finger mechanisms 1 to 4, the first palm portion 8 and the second palm portion 9 cover and grasp an article 101 to be grasped such as a cylindrical cup. In the multi-fingered robot hand according to this embodiment, as shown in FIG. 3, the second palm portion 9 can be bent with respect to the first palm portion 8 by the palm joint 10. This makes it possible to allow a palm surface 21 of the first palm portion 8 and a palm surface 22 of the second palm portion 9 to run along the held article 101, thereby widening the contact area with the held article 101 to realize more stable holding. This grasping form is employed for a tool or an implement provided with a grip such as a frying pan, a hammer and a trowel, or a hose or the like.

Figure 4:
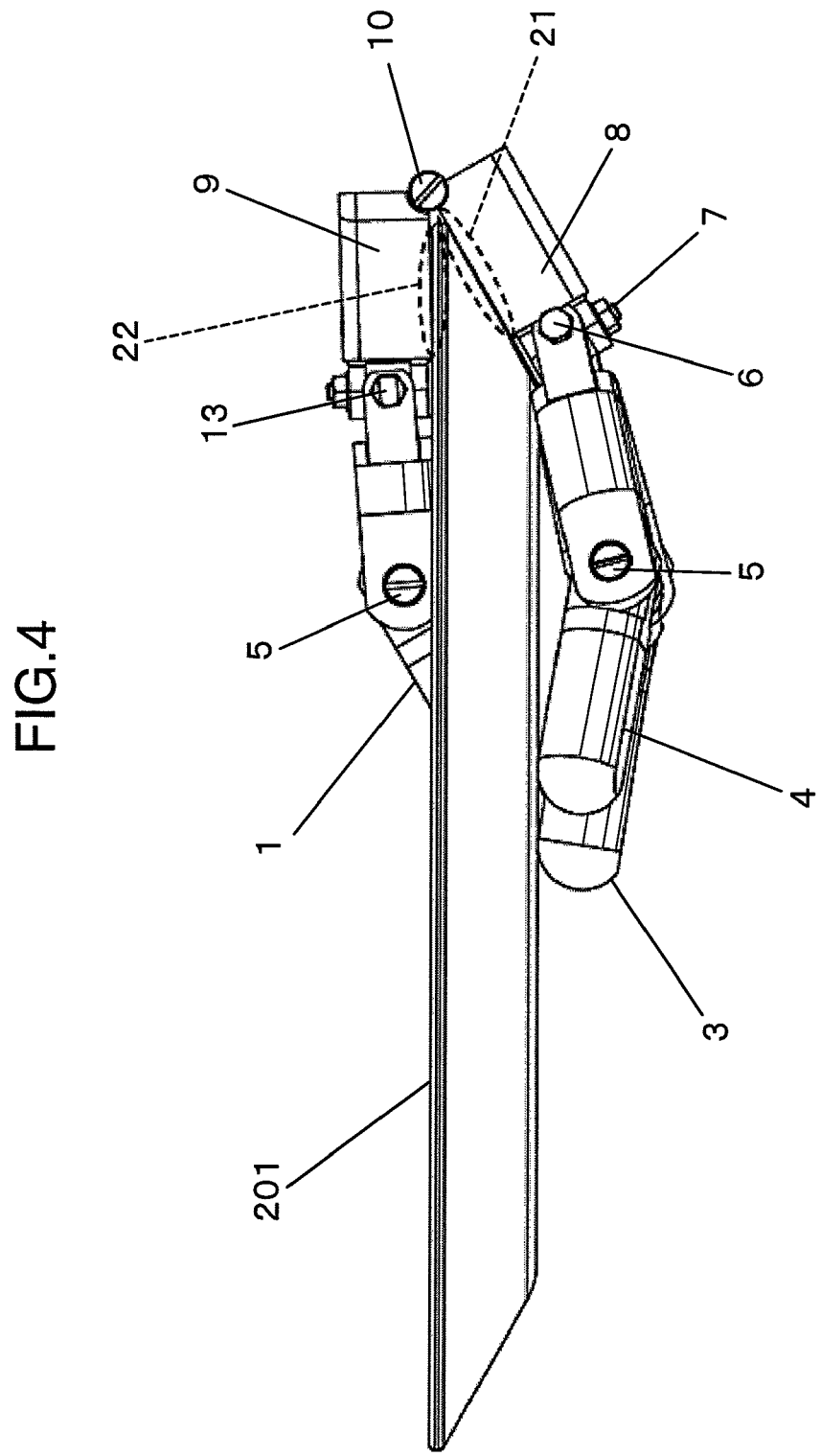
FIG. 4 is a side view showing the multi-fingered robot hand according to the first embodiment grasping a flat plate.

Next, FIG. 4 shows "sandwich grasping"—the four finger mechanisms 1 to 4, the first palm portion 8 and the second palm portion 9 sandwich and grasp an article 201 such as a dish plate. As shown in FIG. 4, the first palm portion 8 and the second palm portion 9 can be bent to sandwich the article 201 between the palm surface 21 of the first palm portion 8 and the palm surface 22 of the second palm portion 9, thereby realizing more stable grasping than nipping the article 201 only by the four finger mechanisms 1 to 4. This grasping form is employed for the plate-shaped article 201 such as a dish plate, a file and a folder.

Figure 5:
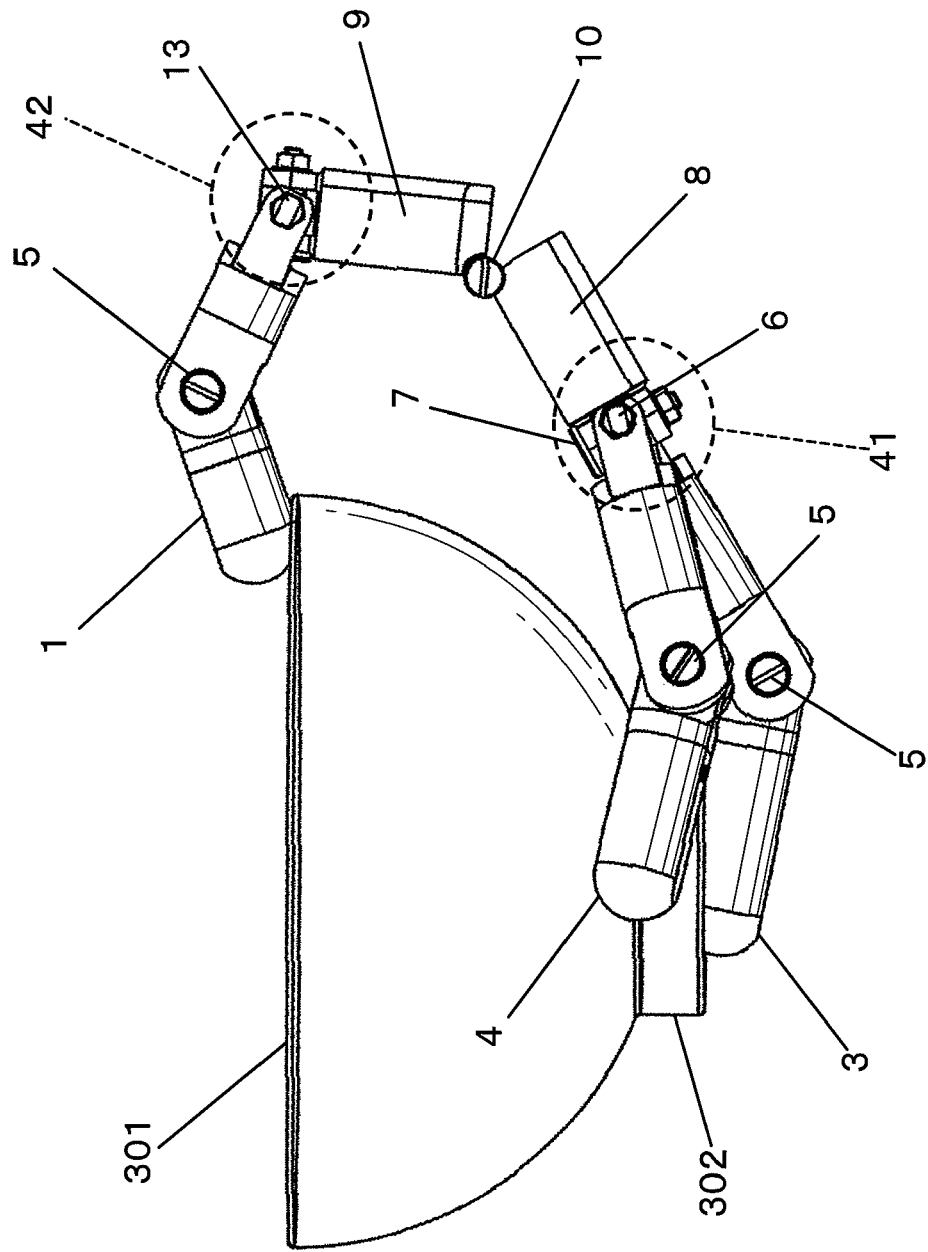
FIG. 5 is a side view showing the multi-fingered robot hand according to the first embodiment grasping a bowl.

Next, FIG. 5 shows "support holding"—the four finger mechanisms 1 to 4 support and hold an article such as a bowl 301. As shown in FIG. 5, the angle of the first palm portion 8 to the second palm portion 9 can be adjusted by the palm joint 10. In other words, an adjustment can be made of the relative positional relationship between root parts (attachment parts) 41 and 42 of the finger mechanisms 1 to 4 provided in the palm portions 8 and 9. A tip part of the finger mechanism 3 supports a bottom rim 302 of the bowl 301 and bears a vertical load and moment of the bowl 301 together with a tip part of the finger mechanism 1. Simultaneously, the finger mechanisms 2 and 4 at both sides of the first palm portion 8 open right and left to support the side parts of the bowl 301, thereby adjusting the right-and-left balance of the bowl 301 to realize stable holding. This holding form is employed for a bowl-shaped article such as a rice bowl, a teacup and a basin.

Figure 6:
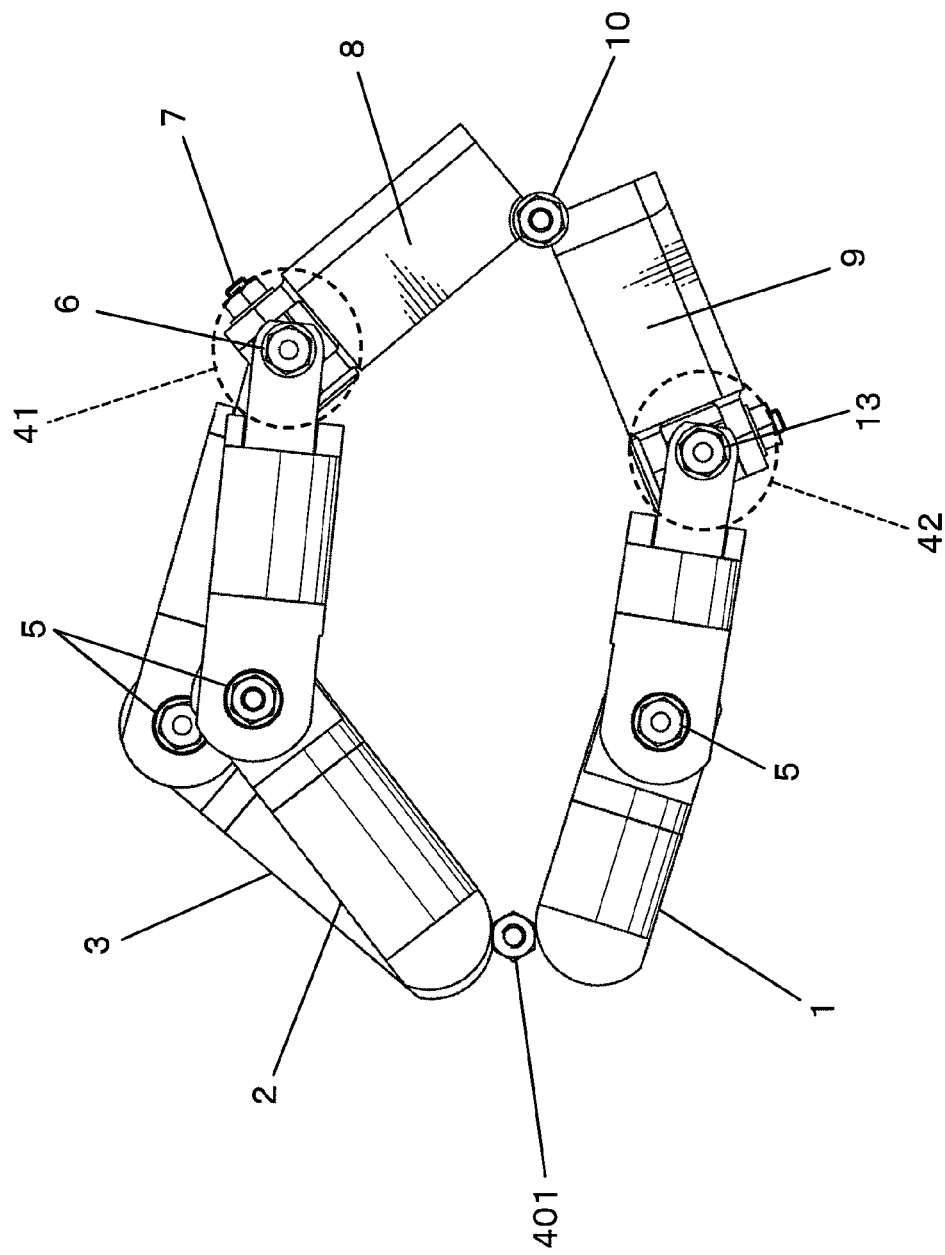
FIG. 6 is a side view showing the multi-fingered robot hand according to the first embodiment grasping a small article.

Next, FIG. 6 shows "nip holding"—two to four such finger mechanisms nip a small article 401 such as a nut. As shown in FIG. 6, the angle of the first palm portion 8 to the second palm portion 9 can be adjusted by the palm joint 10. In other words, an adjustment can be made of the positional relationship between the attachment parts 41 and 42 on the root sides of the finger mechanisms 1 to 4 provided in the palm portions 8 and 9. The finger mechanism 1 and the finger mechanism 3 facing this hold the article 401 between the finger mechanism 2 and the finger mechanism 4. This holding form is employed for the small article 401 such as a nut and a toothpick.

As described so far, according to this embodiment, the angle of the first palm portion 8 to the second palm portion 9 can be freely adjusted, thereby varying the positional relationship between the root joints 12 of the finger mechanisms 2 to 4 on the first-palm portion and the root joint 13 of the finger mechanism 1 on the second-palm portion freely according to an object to be held. This makes it possible to grasp the object easily in a proper posture according to its size or shape. In addition, the palm portions 8 and 9 are folded to sandwich even an object such as a dish plate between the palm portions 8 and 9 and the finger mechanisms 1 to 4, thereby stably holding an article in a wider range. Besides, the palm joint 10 is a joint of the whole robot hand, thereby making it possible to secure the degree of bending freedom necessary for grasping and reduce the number of joints in the finger mechanisms 1 to 4.

Furthermore, according to this embodiment, the rotation axis 10a of the palm joint 10 is parallel to the rotation axes 5a of the bending joints 5, the rotation axes 6a of the bending joints 6 and the rotation axis 13a of the root joint 13. Therefore, the finger mechanisms 1 to 4 can sandwich and hold an object to be grasped from both sides, thereby holding the object stably. In addition, the first palm portion 8 and the second palm portion 9 are folded to grasp even an object such as a dish plate between the palm portions 8 and 9 and the finger mechanisms 1 to 4, thereby realizing stable grasping for the plate-shaped object.

Moreover, according to this embodiment, the middle finger mechanism 3 on the side of the first palm portion 8 and the finger mechanism 1 on the side of the second palm portion 9 are positioned so as to substantially face each other and move substantially on the same plane when grasping an article, thereby realizing stable grasping in nipping the article.

Furthermore, according to this embodiment, each root joint 12 of the right and left finger mechanisms 2 and 4 provided in the first palm portion 8 includes the open-close joint 7 making a lateral open-close motion. Therefore, the two right and left finger mechanisms 2 and 4 of the first palm portion 8 open and close sideward when grasping a plate-shaped article such as a dish plate, a bowl-shaped article such as a rice bowl or the like. This makes it possible to adjust the right-and-left weight balance of the article, thereby realizing more stable grasping.

Moreover, according to this embodiment, each finger mechanism 1 to 4 includes the single bending joint 5, thereby securing the degree of freedom necessary for grasping an article and simplifying the configuration of the robot hand.

In this embodiment, only the root joints 12 and 12 of the finger mechanisms 2 and 4 include the open-close joints 7, 7, however the present invention is not limited to this. For example, in the same way as the finger mechanisms 2 and 4, the root joints 12 and 13 of the finger mechanisms 1 and 3 may include the open-close joints 7, 7. If all the finger mechanisms 1 to 4 are provided with an open-close mechanism, they can grasp even a small article more stably by adjusting the open-close joint 7 on the root side of each finger mechanism to bring the tip of each finger mechanism 1 to 4 around the article. Besides, the open-close motion of each right-and-left finger mechanism 2, 4 provided in the first palm portion 8 may be made independently or interlocked.

As shown in FIGS. 1 to 6, the length of each finger mechanism according to this embodiment is designed to have the relationship of the finger mechanism 3>the finger mechanism 2=the finger mechanism 4>the finger mechanism 1. However, it is not necessarily this relationship, and for example, all the finger mechanisms 1 to 4 may have one and the same length.

Furthermore, in this embodiment, the multi-fingered robot hand includes the four finger mechanisms 1 to 4, but the present invention is not limited to this. For example, it may be appreciated that it includes five or more finger mechanisms, or the first palm portion 8 includes only two right and left finger mechanisms. Besides, according to this embodiment, the finger mechanisms 1 to 4 each include the single bending joint 5, however the present invention is not limited to this. For example, at least one finger mechanism 1 to 4 may include two or more bending joints 5.

Moreover, in this embodiment, the robot hand is connected to a robot manipulator on the back side of the first palm portion 8, but the present invention is not limited to this. For example, it may be appreciated that the robot hand is fixed to a robot manipulator in such a way that the robot manipulator supports the rotation axis 10a of the palm joint 10 connecting the first palm portion 8 and the second palm portion 9, or it is fixed to a robot manipulator on the back side of the second palm portion 9.

Second Embodiment

FIGS. 7A and 7B show a multi-fingered robot hand according to a second embodiment of the present invention. In the second embodiment, the second palm portion 9 according to the first embodiment is provided on the palm surface thereof with an elastic convex member 51, but otherwise it is the same as the first embodiment in the configurations and driving methods.

The elastic convex member 51 shown in FIGS. 7A and 7B covers most of a middle part on the palm surface of the second palm portion 9 and unites with the elastic skin member mentioned in the first embodiment. Similarly to the elastic skin member, it is made of, for example, rubber, urethane, silicone, sponge or the like, and taking its good contact with an article into account, it may desirably have a rubber hardness of approximately 20 to 30 degrees in Hs (hardness spring).

When the multi-fingered robot hand grasps an article, for example shown in FIG. 3 or 4, by making good use of the palm surfaces of the first palm portion 8 and the second palm portion 9, the elastic convex member 51 is useful in grasping the article securely between it and the finger mechanisms 1 to 4 or the other palm portion 8.

As described above, the multi-fingered robot hand according to this embodiment is provided with the elastic convex member 51 on the palm surface of the second palm portion 9, thereby enabling the robot hand to grasp an article more stably using the palm portions 8 and 9 actively.

In this embodiment, the elastic convex member 51 is united with the elastic skin member, however it may be formed as a separate body. Alternatively, it may be appreciated that the elastic convex member 51 is provided in the first palm portion 8 or the both palm portions 8 and 9.

Third Embodiment

FIGS. 8A to 8C show a multi-fingered robot hand according to a third embodiment of the present invention. In this embodiment, the palm portion 9 according to the first embodiment is provided on the palm surface thereof with a bag member 55 which is inflated and deflated with a fluid, but otherwise it is the same as the first embodiment in the configurations and driving methods.

The bag member 55 shown in FIGS. 8A to 8C covers most of a middle part on the palm surface of the second palm portion 9 and is formed as a separate body from the elastic skin member mentioned in the first embodiment. The bag member 55 is made, for example, of an elastic material such as rubber and is filled, for example, with a fluid of a gas such as compressed air or of a liquid such as water.

When grasping an article, for example, as shown in FIG. 3 or FIG. 4, by making good use of the palm surfaces of the first palm portion 8 and the second palm portion 9, the multi-fingered robot hand holds the article securely, as shown in FIG. 8C, between the bag member 55 inflated with a fluid and the finger mechanisms 1 to 4 or the other palm portion 8. On the other hand, when it grasps an article without utilizing the palm surface of the second palm portion 9 so much, as shown in FIG. 8B, the bag member 55 is deflated to thereby impose no restriction on the motion range of the palm joint 10.

As described above, the multi-fingered robot hand according to this embodiment is provided with the bag member 55 which is inflated and deflated with a fluid on the palm surface of the second palm portion 9, thereby enabling the robot hand to grasp an article more stably using the palm portions 8 and 9 actively. On the other hand, when the palm portions 8 and 9 are not used actively, the motion range of the palm joint 10 can be prevented from being restricted.

The bag member 55 may be provided in the first palm portion 8 or the both palm portions 8 and 9.

Fourth Embodiment

FIGS. 9A and 9B show a multi-fingered robot hand according to a fourth embodiment of the present invention. As shown in these figures, in this embodiment, a drive portion varying the connection angle of the first palm portion 8 to the second palm portion 9 is provided which includes a motor 81 generating a driving force and a motor gear 82 attached to the drive shaft of the motor 81.

The first palm portion 8 is provided with a first gear 86a fixed thereon and the second palm portion 9 is provided with a second gear 86b fixed thereon, both gears engaging with each other.

The first gear 86a is arranged at both ends in the width directions of the first palm portion 8. Both first gears 86a are each formed with a through hole, and a transmission shaft 84 corresponding to the axial center of the first gears 86a penetrates this through hole so as to rotate freely. The transmission shaft 84 is provided with a transmission gear 83 fixed thereon which is engaged with the motor gear 82.

Figure 10:
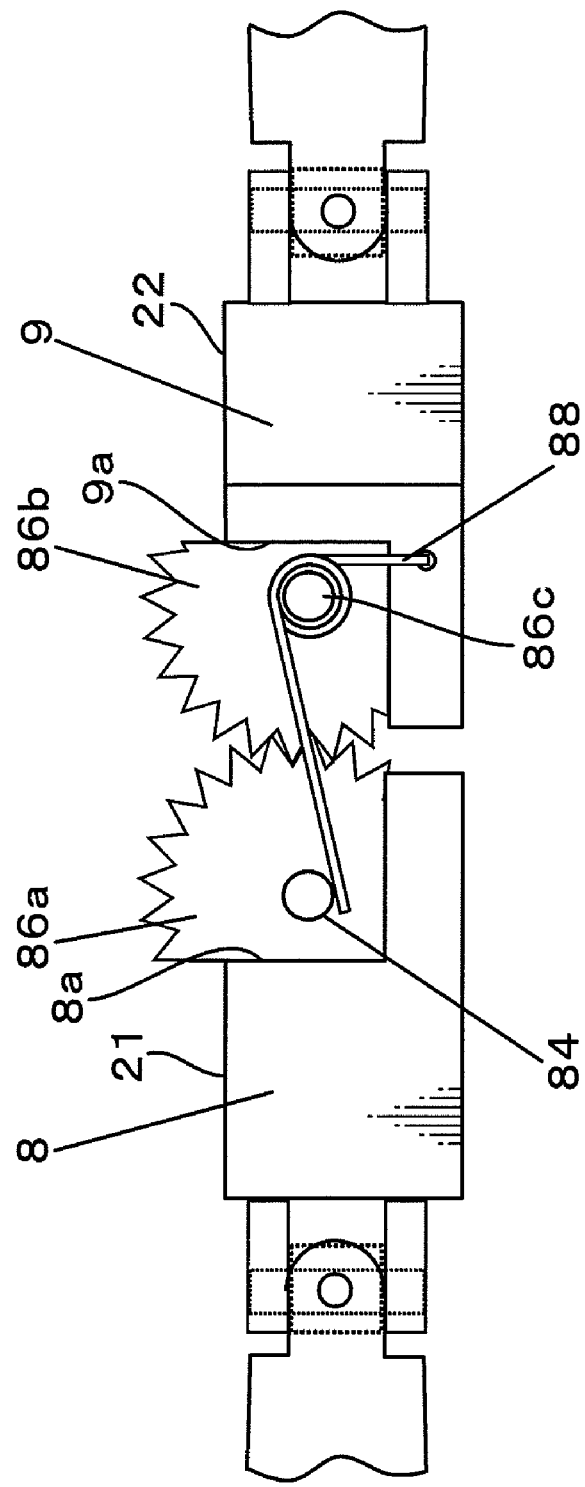
FIG. 10 is a side view of a connecting portion and its vicinity in the multi-fingered robot hand according to the fourth embodiment.

As shown by the enlarged view of FIG. 10, the first palm portion 8 is formed at its edge on the second-palm portion side with a concave portion 8a extending in the width directions of the palm portion 8. The first gear 86a is fixed at both ends of the concave portion 8a. The concave portion 8a is formed by cutting a corner part at the edge on the second-palm portion side of a palm surface 21 of the first palm portion 8 into a rectangular shape in a width-direction section of the first palm portion 8. Therefore, this edge of the first palm portion 8 has two planes crossing substantially at a right angle, one of them being parallel to the palm surface 21.

The first gear 86a is a segment gear having teeth within a predetermined central angle. In other words, it is formed by cutting a spur wheel along two straight lines perpendicular to each other, includes a middle through hole and has teeth within a range of at least 90 degrees. The first gear 86a is coupled onto the concave portion 8a by joining its two perpendicular planes to the two planes of the concave portion 8a in such a way that the first gear 86a protrudes above the palm surface 21 in FIG. 9B.

The second palm portion 9 is formed at its edge on the first-palm portion side with a concave portion 9a extending in the width directions of the palm portion 9. The second gear 86b is fixed at both ends of the concave portion 9a. The concave portion 9a has the same configuration and depth as the concave portion 8a of the first palm portion 8. The second gear 86b protrudes above a palm surface 22 in FIG. 9B.

The second gear 86b is a segment gear having teeth within a predetermined central angle. In other words, it is formed by cutting a spur wheel along two straight lines perpendicular to each other, includes a middle through hole and has teeth within a range of at least 90 degrees. However, the second gear 86b is different in the position of teeth from the first gear 86a. Specifically, the position of each tooth of the first gear 86a with respect to the palm surface 21 of the first palm portion 8 shifts by an equivalent to the half phase of a tooth pitch from the position of each tooth of the second gear 86b with respect to the palm surface 22 of the second palm portion 9. This prevents both palm surfaces 21 and 22 from having any difference in level, even with the palm stretched or with the palm surface 21 of the first palm portion 8 kept flush with the palm surface 22 of the second palm portion 9.

As shown in FIG. 9A, both ends of the transmission shaft 84 protrude outward from the first gear 86a. Each second gear 86b is provided with a shaft portion 86c inserted therein so as to rotate freely which extends in the width directions of the second palm portion 9 and is parallel to the transmission shaft 84. The shaft portion 86c corresponds to the axial center of the second gear 86b and protrudes outward from the second gear 86b.

The connecting portion connecting the first palm portion 8 and the second palm portion 9 includes a swing arm 85 one end of which is fixedly coupled to the transmission shaft 84 and the other end to the shaft portion 86c. Accordingly, the driving force of the motor 81 is transmitted via the motor gear 82, the transmission gear 83 and the transmission shaft 84 to the swing arm 85 to thereby become a driving force for swinging the swing arm 85. The swing arm 85 swings upon the transmission shaft 84. According to the swing width of the swing arm 85, the engagement position of the first gear 86a and the second gear 86b changes, thereby varying the connection angle of the first palm portion 8 and the second palm portion 9. In other words, one of the first palm portion 8 and the second palm portion 9 turns relatively to the other by an equivalent to a swing width of the swing arm 85. For example, in this embodiment, when the palm is fully folded, or when the connection angle of the first palm portion 8 and the second palm portion 9 changes from 180 to zero degrees, the angle of the swing arm 85 is designed to change from the parallel directions to the first palm portion 8 to the perpendicular directions thereto. When the connection angle of the first palm portion 8 and the second palm portion 9 is zero degrees, a space corresponding to the length of the swing arm 85 is secured between the palm surface 21 of the first palm portion 8 and the palm surface 22 of the second palm portion 9.

The shaft portion 86c of the second gear 86b is provided with a biasing member 88 for preventing backlashes. The biasing member 88 is formed by a torsion coil spring, and one end thereof is hooked on the second palm portion 9 and the other end on the transmission shaft 84.

In this embodiment, the drive portion is driven to vary the connection angle of the second palm portion 9 to the first palm portion 8, thereby changing the positional relationship between the root joints 12 on the first-palm portion and the root joint 13 on the second-palm portion.

Furthermore, in this embodiment, the driving force of the motor 81 swings the swing arm 85 to thereby turn the first palm portion 8 relatively to the second palm portion 9. Besides, when the palm is folded, a space corresponding to the size of the first gear 86a and the second gear 86b can be secured between the first palm portion 8 and the second palm portion 9, thereby holding an article to be held in this space.

Moreover, in this embodiment, even when the palm surface 21 of the first palm portion 8 is flush with the palm surface 22 of the second palm portion 9 (the palm is stretched), the first gear 86a and the second gear 86b can be securely engaged. With the palm stretched, there is no difference in level between the palm surface 21 of the first palm portion 8 and the palm surface 22 of the second palm portion 9, thereby stabilizing an article placed on the palm surfaces 21 and 22.

In addition, in this embodiment, the first gear 86a shifts by the half phase of a tooth pitch from the second gear 86b, thereby ensuring the engagement of the first gear 86a and the second gear 86b even if both are attached at the same angle. This makes it possible to suppress complication in working the first palm portion 8 and the second palm portion 9.

In the fourth embodiment, the motor 81 and the transmission shaft 84 for swinging the swing arm 85 are provided in the first palm portion 8. Instead, they may be provided in the second palm portion 9, and in this case, the shaft portion 86c penetrates the first gear 86a so as to rotate freely.

Moreover, in the fourth embodiment, the first gear 86a and the second gear 86b shifting by the half phase of a tooth pitch from each other are employed. However, as shown in FIG. 11, a first gear 86a and a second gear 86b not shifting by any tooth phase from each other may be employed—the first gear 86a and the second gear 86b are formed by a common component.

Instead, the attachment angle of the first gear 86a shifts by an angle equivalent to the half phase of a tooth pitch from the attachment angle of the second gear 86b. With the palm stretched, the angle of the concave portion 8a of the first palm portion 8 to the concave portion 9a of the second palm portion 9 shifts by an angle equivalent to the half phase of a tooth pitch from each other. In the example of this figure, one plane of the concave portion 8a of the first palm portion 8 is parallel to the palm surface 21 while one plane of the concave portion 9a of the second palm portion 9 is inclined to the palm surface 22. Conversely, one plane of the concave portion 9a of the second palm portion 9 may be parallel to the palm surface 22 while one plane of the concave portion 8a of the first palm portion 8 may be inclined to the palm surface 21.

According to this aspect, the first gear 86a and the second gear 86b can be securely engaged even with the palm stretched, and the first gear 86a and the second gear 86b can share the common component with each other.

Figure 12A:
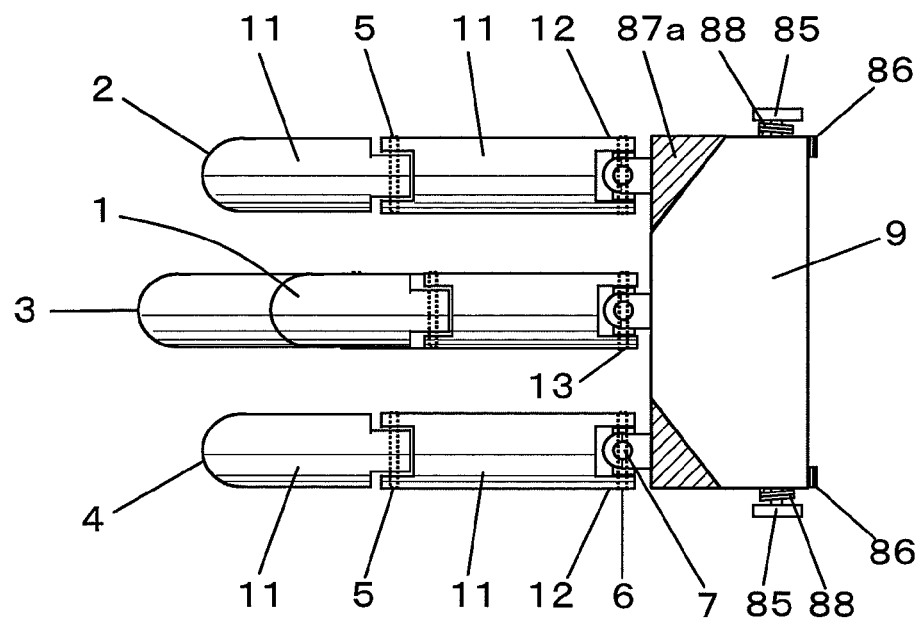
FIGS. 12A and 12B are front and side views, respectively, of a variation of the multi-fingered robot hand according to the fourth embodiment.
Figure 12B:
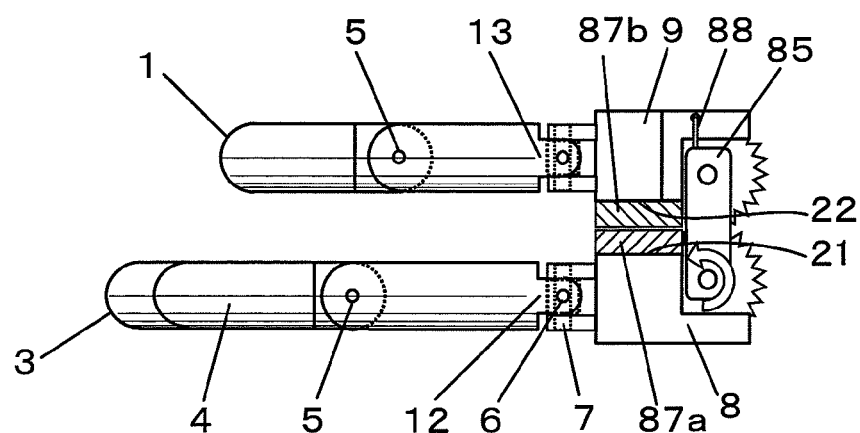

In addition, as shown in FIGS. 12A and 12B, both palm portions 8 and 9 are provided with elastic convex members 87a and 87b, respectively. The elastic convex members 87a and 87b are made of, for example, rubber, urethane, silicone, sponge or the like. The elastic convex member 87a is stuck on the whole palm surface 21 of the first palm portion 8 and the elastic convex member 87b is stuck on the whole palm surface 22 of the second palm portion 9.

According to this aspect, when the palm is folded, the elastic convex members 87a and 87b come into the space corresponding to the size of the gears 86a and 86b or the space corresponding to the length of the swing arm 85 and are deformed to moderate the pressing force for an article to be held, thereby preventing the article from being damaged. Some changes in shape of the elastic convex members 87a and 87b enlarges the contact area with the article, thereby enabling the robot hand to grasp the article more stably.

Fifth Embodiment

Figure 13:
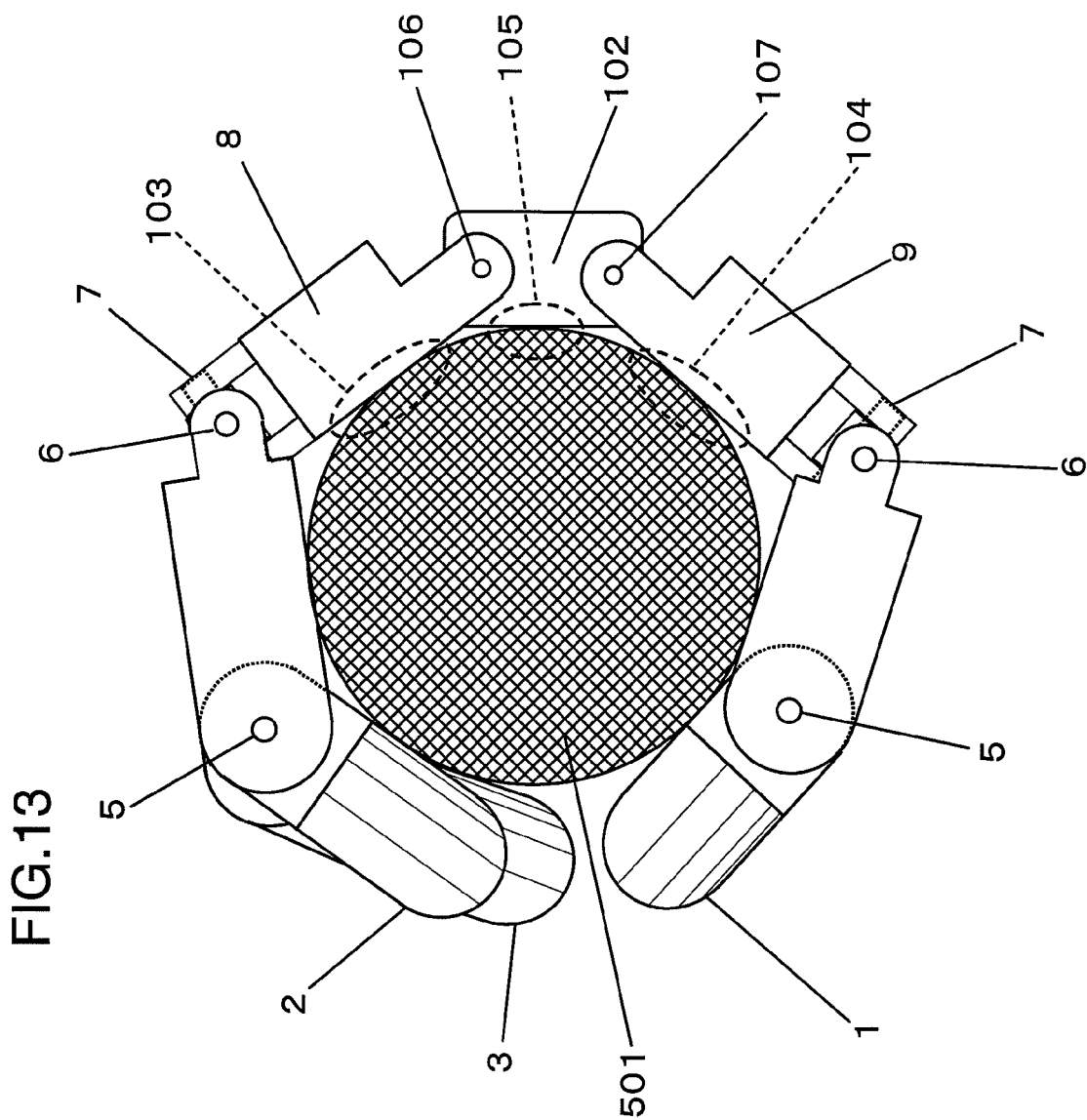
FIG. 13 is a side view of a multi-fingered robot hand according to a fifth embodiment of the present invention.
Figure 15A:
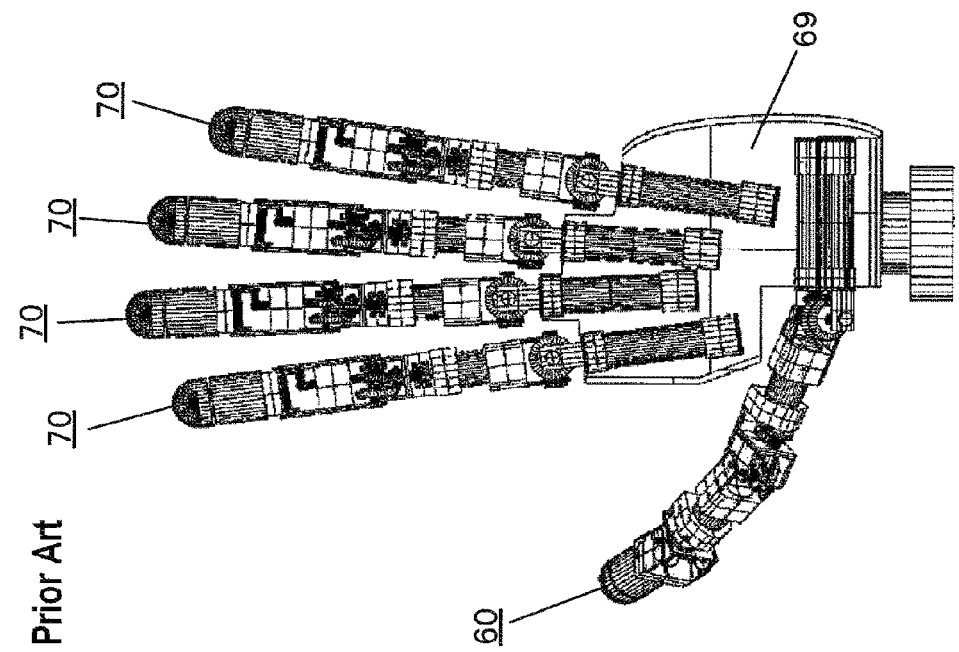
FIG. 15A is a perspective view showing a configuration of a conventional single-finger mechanism of a human-like multi-fingered robot hand.
Figure 15B:
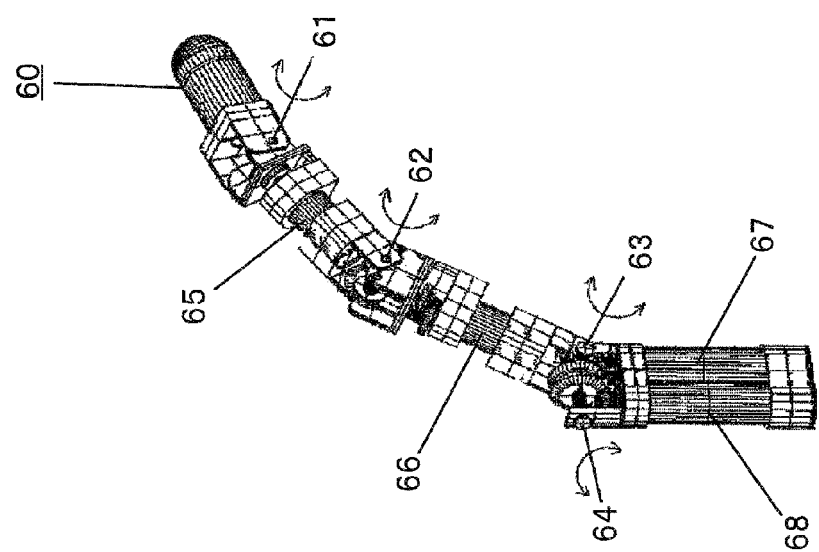
FIG. 15B is a front view of the whole human-like multi-fingered robot hand.
Figure 16:
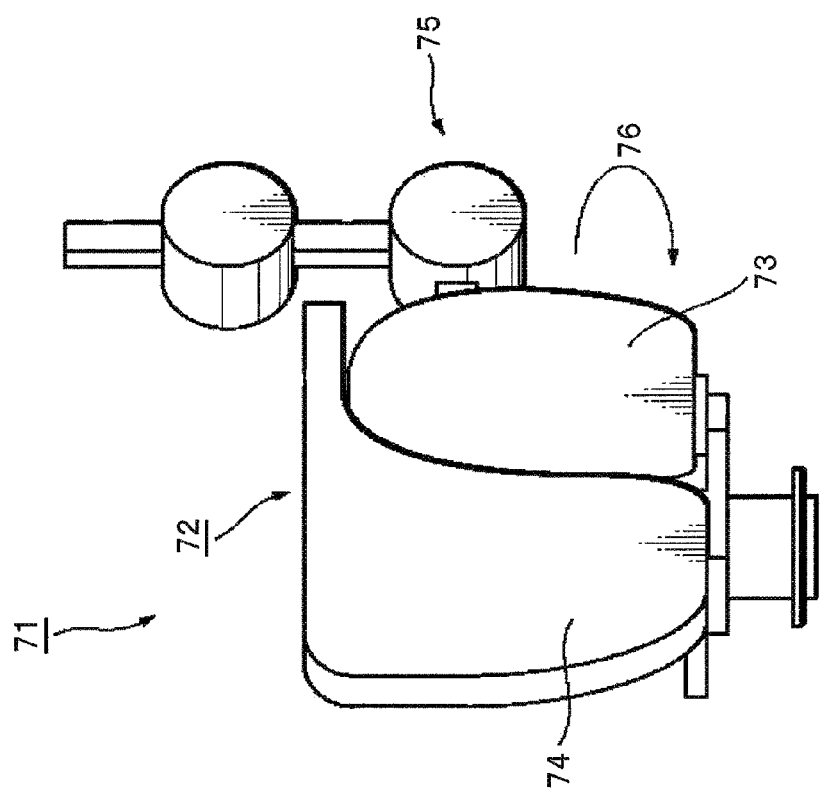
FIG. 16 is a perspective view showing a configuration of a conventional robot hand provided with a ball of the thumb.

In a fifth embodiment of the present invention, the connecting portion connecting the first palm portion 8 and the second palm portion 9 includes a plurality of palm joints, and specifically, as shown in FIG. 13, a third palm portion 102, a first palm joint 106 and a second palm joint 107. The first palm joint 106 connects the first palm portion 8 and the third palm portion 102 and the second palm joint 107 connects the second palm portion 9 and the third palm portion 102. The third palm portion 102 has a length, for example, substantially equal to the swing arm 85 according to the fourth embodiment. The first palm joint 106 and the second palm joint 107 each have, for example, a rotation axis for rotating relatively which is parallel to the rotation axes 5a and 6a of the bending joints 5 and 6.

This configuration allows not only a palm surface 103 of the first palm portion 8 and a palm surface 104 of the second palm portion 9 but also a palm surface 105 of the third palm portion 102 to run along an article 501 to be held. In other words, the connection angles at the palm joints 106 and 107 can be freely varied according to the article 501, thereby stably grasping even objects of different sizes by effectively utilizing the palm surface having a larger contact area.

Instead of two such palm joints, three or more may be provided, and the other configurations and the like are the same as the first embodiment.

Sixth Embodiment

A multi-fingered robot hand according to a sixth embodiment of the present invention, as shown in FIGS. 14A and 14B, is provided with a drive portion of the open-close joint 7.

The drive portion of the open-close joint 7 includes a motor 113, worm wheels 107 and 108, worms 109 and 110, a shaft 111, gears 112, 114 and 115 and support walls 116 and 117. The support walls 116 and 117 are fixed on the first palm portion 8 and support the shaft 111 rotatably. The shaft 111 extends in the width directions of the first palm portion 8 and is provided with the gear 112 fixed thereon. The driving force of the motor 113 is transmitted from the motor gear 114 fixed on its drive shaft via the gear 115 to the gear 112.

The shaft 111 is also provided with the worms 109 and 110 fixed thereon which have a helix in the opposite direction to each other. The worm wheel 107 is fixed to the root of the finger mechanism 2 and engaged with the worm 110 while the worm wheel 108 is fixed to the root of the finger mechanism 4 and engaged with the worm 109.

Therefore, the motor 113 is driven to rotate the shaft 111 interlocked thereto and the worms 109 and 110 having the opposite-direction helices, thereby turning the worm wheels 108 and 107 engaged therewith in the opposite direction to each other and opening or closing the finger mechanisms 4 and 2, respectively.

The other configurations and the like are the same as the first embodiment.

SUMMARY OF THE EMBODIMENTS

The embodiments of the present invention will be below summarized.

(1) In the embodiments, the angle of the first palm portion to the second palm portion can be freely adjusted, thereby freely varying the positional relationship between the first root joints on the first-palm portion and the second root joint on the second-palm portion according to an object to be held. This makes it possible to grasp the object easily in a proper posture according to its size or shape. Besides, the connecting portion is a joint of the whole robot hand, thereby making it possible to secure the degree of bending freedom necessary for grasping and reduce the number of joints in the finger mechanisms.

(2) In the multi-fingered robot hand, it is preferable that: the connecting portion has a rotation axis for varying the connection angle of the second palm portion to the first palm portion; the first root joint has a rotation axis for bending the corresponding finger mechanism to the palm side; the second root joint has a rotation axis for bending the corresponding finger mechanism to the palm side; and the rotation axes are all substantially parallel to each other. According to this aspect, the finger mechanisms can sandwich and grasp an object to be grasped from both sides, thereby grasping the object stably. In addition, the first palm portion and the second palm portion are folded to grasp even an object such as a dish plate between the palm portions and the finger mechanisms, thereby realizing stable grasping for the plate-shaped object.

(3) In the multi-fingered robot hand, preferably: the first root joint may be connected to the surface of the first palm portion which is opposite to the connection surface of the first palm portion to the connecting portion; and the second root joint may be connected to the surface of the second palm portion which is opposite to the connection surface of the second palm portion to the connecting portion.

(4) It is preferable that: three finger mechanisms are connected in array to the first palm portion; and the middle finger mechanism of the finger mechanisms connected to the first palm portion and one finger mechanism connected to the second palm portion are arranged in such a way that both finger mechanisms move substantially on the same plane when bent. According to this aspect, when grasping an article, the middle finger mechanism on the first-palm portion and the finger mechanism on the second-palm portion are positioned so as to substantially face each other, thereby realizing stable grasping in nipping the article.

(5) Preferably: three finger mechanisms may be connected in array to the first palm portion; the finger mechanisms connected to the first palm portion and the finger mechanism connected to the second palm portion each may include a bending joint for bending the finger mechanism around an axis parallel to the rotation axis; and the first root joints of the finger mechanisms at both ends among the finger mechanisms connected to the first palm portion may each include an open-close joint for moving the finger mechanism perpendicularly to the bending directions by the bending joint. According to this aspect, when grasping a plate-shaped article such as a dish plate, a bowl-shaped article such as a rice bowl or the like, the two right and left finger mechanisms of the first palm portion open and close so as to move their tips sideward. This makes it possible to adjust the right-and-left weight balance of the article, thereby realizing more stable grasping.

(6) It is preferable that: the plurality of finger mechanisms each include a bending joint for bending the finger mechanism around an axis parallel to the rotation axis; and the first and second root joints each include an open-close joint for moving the finger mechanism perpendicularly to the bending directions by the bending joint. According to this aspect, the multi-fingered robot hand can grasp even a small article more stably by adjusting the open-close joint on the root side of each finger mechanism to bring the tip of each finger mechanism around the article. Besides, the open-close mechanisms can be adjusted according to the weight balance of an article, thereby realizing stable grasping.

(7) Each finger mechanism may also include one as the bending joint. According to this aspect, the degree of freedom necessary for grasping an article can be secured and the configuration of the robot hand becomes simpler.

(8) At least one of the first and second palm portions may include an elastic convex member on the palm surface. According to this aspect, when the pair of palm portions sandwiches an article or when the finger mechanisms and the palm portions grasp it, the elastic convex member is useful in grasping the article securely, thereby enabling the robot hand to grasp it more stably.

(9) At least one of the first and second palm portions may also include a bag member on the palm surface which is inflated and deflated with a fluid. According to this aspect, when the pair of palm portions sandwiches an article or when the finger mechanisms and the palm portions grasp it, the inflated bag member is useful in holding the article securely, thereby enabling the robot hand to grasp it more stably. When the inflated bag member is not needed, it is deflated to thereby impose no restriction on the motion range of the connecting portion.

(10) A drive portion may also be provided which varies the connection angle of the second palm portion to the first palm portion. According to this aspect, the drive portion is driven to vary the angle of the second palm portion to the first palm portion, thereby changing the positional relationship between the first root joints and the second root joint.

(11) In this aspect, it is preferable that: the connecting portion includes a swing arm pivoted so as to swing to one of the first palm portion and the second palm portion, the swing arm swinging the other of the first palm portion and the second palm portion with respect to the one thereof; and the drive portion includes a motor generating a driving force for swinging the swing arm. According to this aspect, the driving force of the motor swings the swing arm to thereby swing the other of the first palm portion and the second palm portion relatively to the one thereof.

(12) In this aspect, it is preferable that: a first gear is fixed to the first palm portion; a second gear engaging with the first gear is fixed to the second palm portion; and the engagement position of the first gear and the second gear changes according to the swing width of the swing arm and the other of the first palm portion and the second palm portion swings relatively to the one thereof. According to this aspect, while the engagement position of the first gear and the second gear is changing as the swing arm swings, one of the first palm portion and the second palm portion turns relatively to the other thereof by an equivalent to a swing width of the swing arm. When the palm is folded, a space corresponding to the size of the first gear and the second gear can be secured between the first palm portion and the second palm portion, thereby holding an article to be held in this space.

(13) Preferably: the position of each tooth of the first gear with respect to the palm surface of the first palm portion may also shift by an equivalent to the half phase of a tooth pitch from the position of each tooth of the second gear with respect to the palm surface of the second palm portion. According to this aspect, even when the palm surface of the first palm portion is flush with the palm surface of the second palm portion (the palm is stretched), the first gear and the second gear can be securely engaged. With the palm stretched, there is no difference in level between the palm surface of the first palm portion and the palm surface of the second palm portion, thereby stabilizing an article placed on the palm surfaces.

(14) In this aspect, it is preferable that: the first gear and the second gear are formed by a common component; and the attachment angle of the first gear to the first palm portion shifts by an angle equivalent to the half phase of a tooth pitch from the attachment angle of the second gear to the second palm portion. According to this aspect, the first gear and the second gear can be securely engaged even with the palm stretched, and the first gear and the second gear can share the common component with each other.

(15) On the other hand, both the first gear and the second gear may also be a segment gear having teeth within a predetermined central angle, and the first gear and the second gear may also be formed so that the teeth of the first gear shift by the half phase from the teeth of the second gear. According to this aspect, the engagement of the first gear and the second gear can be ensured even if both are attached at the same angle, thereby suppressing complication in working the first palm portion and the second palm portion.

(16) Preferably: the connecting portion may include at least one palm joint.

(17) The connecting portion may include: a third palm portion; a first palm joint connecting the first palm portion and the third palm portion; and a second palm joint connecting the second palm portion and the third palm portion. According to this aspect, the connection angles at the palm joints can be freely varied according to an article to be grasped, thereby stably grasping even objects of different sizes by effectively utilizing the palm surface having a larger contact area.

As described so far, the multi-fingered robot hand according to the present invention has a minimum required number of joints in finger mechanisms and is capable of stably grasping a variety of articles.

INDUSTRIAL APPLICABILITY

Advantageously, the multi-fingered robot hand according to the present invention is capable of grasping a variety of articles skillfully and stably despite its configuration having a less degree of freedom. Therefore, it is useful as an end-effector for an industrial or household robot handling various and diverse articles, an artificial hand and the like.

The invention claimed is:
1. A multi-fingered robot hand comprising:
a plurality of finger mechanisms;
a first palm portion provided with at least one of the finger mechanisms connected by a first root joint;
a second palm portion provided with at least one of the finger mechanisms connected by a second root joint; and
a connecting portion connecting the first palm portion and the second palm portion, wherein:
the connecting portion has a rotation axis for varying a connection angle of the second palm portion to the first palm portion and permits a variation in the connection angle of the second palm portion to the first palm portion;
the first root joint has a rotation axis for bending the corresponding finger mechanism to its palm side;
the second root joint has a rotation axis for bending the corresponding finger mechanism to its palm side;
the rotation axes are all substantially parallel to each other;
the plurality of finger mechanisms includes three finger mechanisms connected in array to the first palm portion; and
a middle finger mechanism of the finger mechanisms connected to the first palm portion and one finger mechanism connected to the second palm portion are arranged in such a way that both finger mechanisms move substantially on the same plane when bent.

2. The multi-fingered robot hand according to claim 1, wherein:
the first root joint is connected to a surface of the first palm portion which is opposite to a connection surface of the first palm portion to the connecting portion; and the second root joint is connected to a surface of the second palm portion which is opposite to a connection surface of the second palm portion to the connecting portion.

3. The multi-fingered robot hand according to claim 1, wherein:
   each of the finger mechanisms connected to the first palm portion has a first root joint with a rotation axis for bending the corresponding finger mechanism to its palm side;
   the finger mechanisms connected to the first palm portion and the finger mechanism connected to the second palm portion each include a bending joint for bending the finger mechanism around an axis parallel to the rotation axis of the corresponding root joint; and
   the first root joints of the finger mechanisms at both ends of the finger mechanisms connected to the first palm portion each include an open-close joint for moving the finger mechanism perpendicularly to bending directions of the corresponding bending joint.

4. The multi-fingered robot hand according to claim 1, wherein:
   the finger mechanisms each include a bending joint for bending the finger mechanism around an axis parallel to the rotation axis of the first root joint; and
   the first and second root joints each include an open-close joint for moving the finger mechanism perpendicularly to bending directions of the bending joints.

5. The multi-fingered robot hand according to claim 1, wherein each finger mechanism includes at least one bending joint.

6. The multi-fingered robot hand according to claim 1, wherein at least one of the first and second palm portions includes an elastic convex member on a palm surface.

7. The multi-fingered robot hand according to claim 1, wherein at least one of the first and second palm portions includes a bag member on a palm surface which is inflated and deflated with a fluid.

8. The multi-fingered robot hand according to claim 1, wherein a drive portion is provided which varies the connection angle of the second palm portion to the first palm portion.

9. The multi-fingered robot hand according to claim 8, wherein:
   the connecting portion includes a swing arm pivoted so as to swing to one of the first palm portion and the second palm portion, the swing arm swinging the other of the first palm portion and the second palm portion with respect to the one of the first palm portion and the second palm portion;
   the drive portion includes a motor generating a driving force for swinging the swing arm;
   a first gear is fixed to the first palm portion;
   a second gear engaging with the first gear is fixed to the second palm portion; and
   an engagement position of the first gear and the second gear changes according to a swing width of the swing arm and the other of the first palm portion and the second palm portion swings and turns relatively to the one of the first palm portion and the second palm portion.

10. The multi-fingered robot hand according to claim 9, wherein:
   a position of each tooth of the first gear with respect to the palm surface of the first palm portion shifts by an angle equivalent to a half phase of a tooth pitch from a position of each tooth of the second gear with respect to the palm surface of the second palm portion; and
   the first and second palm portions are arranged in such a way that the surfaces thereof on the palm side are substantially flush with each other at the connection angle of 180°.

11. The multi-fingered robot hand according to claim 10, wherein:
   the first gear and the second gear are formed by a common component; and
   an attachment angle of the first gear to the first palm portion shifts by an angle equivalent to the half phase of the tooth pitch from the attachment angle of the second gear to the second palm portion.

12. The multi-fingered robot hand according to claim 10, wherein:
   the first gear and the second gear are both a segment gear having teeth within a predetermined central angle;
   the first gear and the second gear are formed so that the teeth of the first gear shift by the half phase from the teeth of the second gear.

13. The multi-fingered robot hand according to claim 1, wherein the connecting portion includes at least one palm joint.

14. The multi-fingered robot hand according to claim 13, wherein the connecting portion includes:
   a third palm portion;
   a first palm joint connecting the first palm portion and the third palm portion; and
   a second palm joint connecting the second palm portion and the third palm portion.

* * * * *